(12) United States Patent
Nicholson

(10) Patent No.: US 9,459,199 B2
(45) Date of Patent: Oct. 4, 2016

(54) HUMIDITY SENSING SYSTEM

(71) Applicant: Stewart Nicholson, Doylestown, PA (US)

(72) Inventor: Stewart Nicholson, Doylestown, PA (US)

(73) Assignee: Primex Process Specialists, Inc., Doylestown, PA (US)

( * ) Notice: Subject to any disclaimer, the term of this patent is extended or adjusted under 35 U.S.C. 154(b) by 364 days.

(21) Appl. No.: 14/021,554

(22) Filed: Sep. 9, 2013

(65) Prior Publication Data

US 2014/0076027 A1 Mar. 20, 2014

Related U.S. Application Data

(60) Provisional application No. 61/700,961, filed on Sep. 14, 2012.

(51) Int. Cl.
*G01N 19/10* (2006.01)
*G01N 1/22* (2006.01)
*G01N 25/56* (2006.01)

(52) U.S. Cl.
CPC ............ *G01N 19/10* (2013.01); *G01N 1/2247* (2013.01); *G01N 25/56* (2013.01)

(58) Field of Classification Search
CPC .............................. G01N 1/2247; G01N 19/10
See application file for complete search history.

(56) References Cited

U.S. PATENT DOCUMENTS

| | | | | |
|---|---|---|---|---|
| 3,561,378 A | * | 2/1971 | Fabry | F23G 5/165 110/187 |
| 3,766,715 A | * | 10/1973 | Archer | G01N 27/16 55/283 |
| 3,886,797 A | * | 6/1975 | Bauer | G01N 25/64 73/29.02 |
| 4,616,508 A | * | 10/1986 | Jorn | G01N 1/286 73/818 |
| 5,016,472 A | * | 5/1991 | Amrhein | G01N 25/64 73/29.02 |
| 5,385,043 A | * | 1/1995 | Fitch | G01N 15/0618 110/179 |
| 5,460,041 A | | 10/1995 | Andes et al. | |
| 5,712,421 A | * | 1/1998 | Raisanen | G01N 7/16 73/19.1 |
| 5,824,919 A | * | 10/1998 | Hansen | G01N 1/22 73/863.12 |
| 8,313,555 B2 | | 11/2012 | Petty | |
| 8,329,125 B2 | | 12/2012 | Nicholson | |
| 2003/0132380 A1 | * | 7/2003 | Miller | H01J 49/0018 250/286 |
| 2006/0156927 A1 | * | 7/2006 | Udagawa | B01D 46/0001 96/417 |
| 2014/0238348 A1 | * | 8/2014 | Pursifull | F02M 25/0221 123/434 |
| 2014/0238370 A1 | * | 8/2014 | Pursifull | F02D 41/005 123/690 |

* cited by examiner

*Primary Examiner* — Andre Allen
(74) *Attorney, Agent, or Firm* — Gregory J. Gore

(57) ABSTRACT

A humidity sensor and filter assembly are housed within a cylindrical barrel that is positioned in a process gas stream such as combustion flue gas. A portion of sample flue gas is conducted through the barrel and the filter assembly past the sensor located inside the filter so that accurate humidity measurements can be taken. Unwanted flue gas particulate matter accumulated on the outside surface of the filter is ejected by pulsed purge gas admitted into the filter to reverse the flow through the filter. In one embodiment a heat exchange chamber preheats the purge gas. In another embodiment the pulsed purge is supplied by a reciprocal piston contiguous with the internal volume of the filter that reverses the flow through the filter using the process gas.

30 Claims, 3 Drawing Sheets

HUMIDITY SENSING SYSTEM

RELATED APPLICATIONS

This application is related to provisional patent application Ser. No. 61/700,961 filed Sep. 14, 2012 entitled "Humidity Sensing System" priority from which is hereby claimed.

FIELD OF THE INVENTION

The present invention relates to continuous measurement of gas humidity in industrial ducts and vessels in which particulate matter with cohesive or adhesive properties is present in the gas stream. For the purpose of this invention, the term "humidity" is also intended to include various other parameters in which gas moisture content is a necessary calculation input, such as: adiabatic saturation temperature, dew point temperature and wet-bulb temperature.

BACKGROUND

Many industrial processes can be improved by continuous, precise and reliable measurement of gas humidity. In processes such as flue gas desulfurization (FGD), solid particles with cohesive or adhesive properties are present in the gas stream at temperatures approaching the adiabatic saturation temperature; in these cases, continuous measurement of gas humidity using systems of the prior art is problematic. Common problems include condensation, agglomeration, adhesion and accumulation of solids on the humidity sensor causing interference with signal continuity, precision and reliability. These problems may be compounded by the presence of aqueous chemical compounds, such as calcium chloride, that exist in liquid form at temperatures substantially above the adiabatic saturation temperature.

The FGD process is an example in which continuous, precise and reliable measurement of gas humidity can be advantageous. FGD systems are intended to remove pollutants including sulfur dioxide, hydrochloric acid and mercury produced during the combustion of organic matter such as coal, biomass or municipal waste. More specifically, gas humidity and related parameters (such as dew point temperature, wet bulb temperature and adiabatic saturation temperature) are well known to affect pollutant removal rate, reagent consumption and corrosion rate at specific locations within "dry", "semi-dry" or "spray dryer" type FGD systems. At these locations, most notably at the exit of the absorber vessel upstream of the particulate removal device, continuous humidity sensing systems of the prior typically fail due to agglomeration of particulate matter and liquids (such as saturated aqueous solutions of calcium chloride) that may exist above the adiabatic saturation temperature of water.

Therefore, there is a need in the art for a humidity sensing system that is fully automatic, accurate, precise, reliable and cost effective to operate in particulate laden gas streams at temperatures approaching the adiabatic saturation temperature.

SUMMARY OF THE INVENTION

To meet the need in the art as explained above, a humidity sensing system has been devised that automatically and continuously separates solid particulate matter from the process gas stream around the sensor element thereby enabling the system to provide humidity data that is sufficiently accurate, precise, reliable and cost effective to operate in particulate laden process gas streams at temperatures approaching the adiabatic saturation temperature. This purpose is achieved by locating the humidity sensor within a filtration apparatus that separates particulate matter from the gas stream continuously and automatically. The humidity sensor and filter assembly are housed within a cylindrical barrel that is positioned in the process gas stream. A portion of sampled process gas is conducted through the barrel and the filter assembly past the sensor so that measurements can be taken. In one embodiment, in order that particulate matter that may have accumulated on the outside surface of the filter media can be removed, purge gas is conditioned and then intermittently admitted into the internal filter volume to reverse the flow through the filter to eject the accumulated matter.

More specifically, in but one embodiment of the invention a device for sensing humidity in a stream of power plant combustion process flue gas comprises an elongate cylindrical barrel having a gas inlet port at a distal end for continuously receiving a slipstream of flue gas. The barrel is placed directly into the flue gas stream perpendicular to the flow so that the received gas is conducted through a protective filter assembly that houses a humidity sensor. Received gas then exits the barrel through a laterally disposed outlet port in the sidewall of the barrel. The barrel also contains a series of purge gas conditioning chambers through which purge gas passes from a source of purge gas into an upstream end and out of a downstream end. The conditioning chambers cause the purge gas temperature and humidity to approach equilibrium with the slipstream flue gas temperature. The downstream end of the final conditioning chamber is in fluid communication with the internal volume of the filter assembly so that purge gas can pass into the filter reversing the flow of gas through the filter to clean its outside surface of any residual accumulated matter that may have been separated from the slipstream flue gas. A baffle may be employed inside the conditioning chambers to enhance equalization of purge gas temperature with flue gas temperature. For example, a spiral helix may be used to increase heat conduction and contact surface area of the purge gas flow through the conditioning chambers.

An accumulator is preferably also located within the barrel for temporarily holding a volume of pressurized purge gas. The accumulator is in fluid communication with a conditioning chamber such that purge gas is intermittently dischargeable into the conditioning chamber during a pulsed purge cycle thereby forcing conditioned purge gas through the filter assembly. The pulse cycles are controlled by valve means which regulate gas flow between the accumulator and conditioning chamber. The valve means are operated by a controller which by way of example may time a purge pulse at a frequency of once an hour for a duration of 0.3 seconds but are application specific. Optimization of these timing variables is critical to the proper functioning of the invention.

In yet another embodiment of the invention a positive displacement piston is reciprocally operable within the barrel to reverse the flue gas flow direction thereby intermittently ejecting accumulated matter from the filter media surface. The piston is preferably driven by compressed air and a return spring.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

DESCRIPTION OF THE PREFERRED EMBODIMENT

Figure 1:
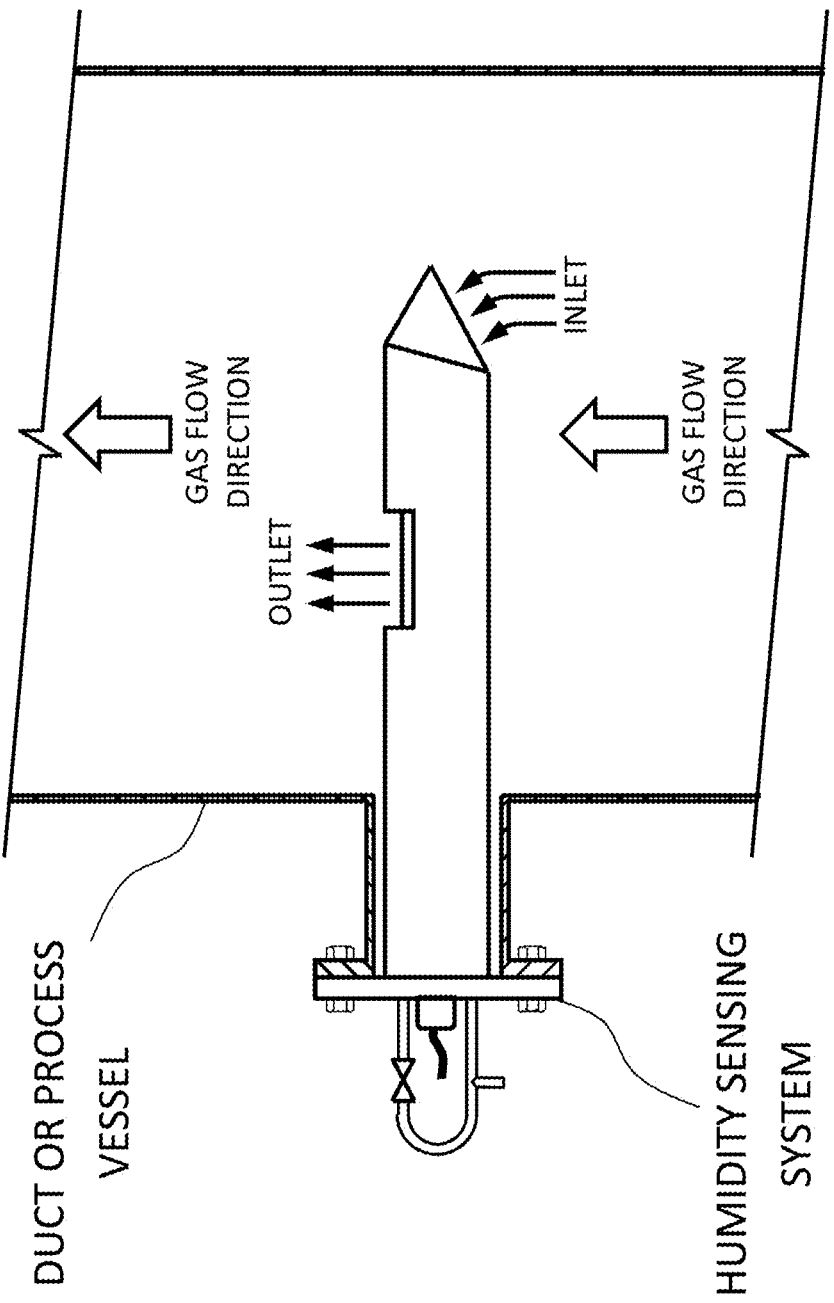
FIG. 1 is a plan view of the invention positioned with a process gas duct.

As shown in FIG. 1 the system is contained within a barrel-like cylinder and placed into a process gas stream arranged with its longitudinal axis perpendicular to the gas flow direction. Process gas enters the system through an inlet port (facing toward the gas stream at the outboard end of the cylinder) and exits from the system through an outlet port in the side of the cylinder (facing away from the gas stream). These inlet and outlet ports are specifically arranged to induce process gas flow through the assembly without the need for auxiliary induction. Generally arranged as shown in FIG. 1, two embodiments of the invention are described below.

Figure 2:
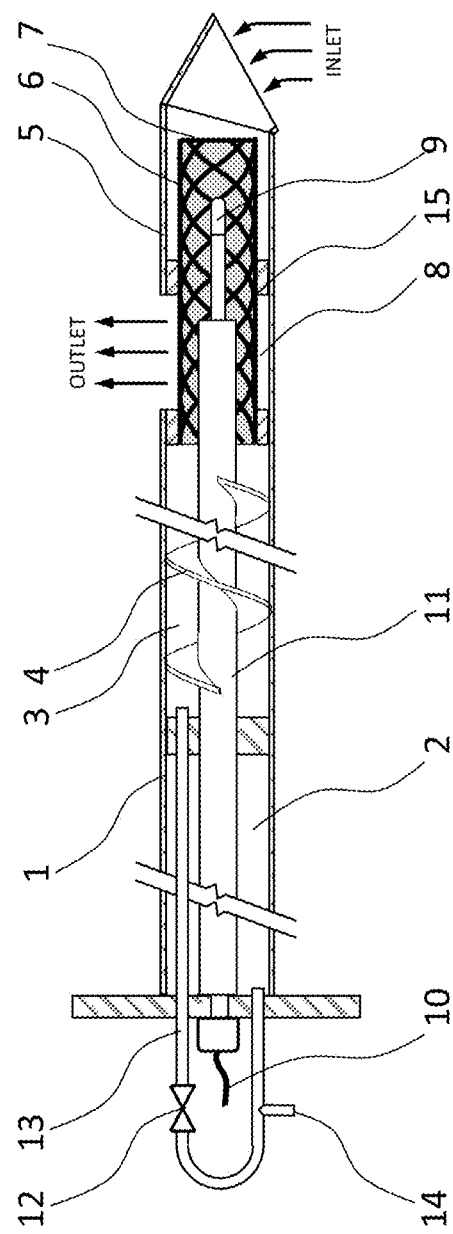
FIG. 2 is a plan cross-section view.

The first embodiment of this invention is illustrated in the cross sectional diagram of FIG. 2. Referring to FIG. 2, a filtration duct 5 houses a filter assembly 6. The filter assembly 6 is comprised of a filter cage and a filter bag, the exterior of which is preferably coated with a PTFE membrane to reduce adhesion of solid particles contained within the process gas. The filtration duct 5 is located in the process gas stream such that a continuous flow of process gas is induced to flow past the humidity sensor element 9 by the differential pressure existing between the high pressure chamber 7 surrounding the filter assembly 6 at the inlet port and the low pressure chamber 8 surrounding the filter assembly 6 at the outlet port. The high pressure chamber 7 and low pressure chamber 8 are separated by a barrier 15 surrounding the exterior of the filter assembly 6.

Referring again to FIG. 2, the sampling and filtration apparatus is shown joined to other elements of the invention held within a cylindrical barrel 1 which forms the main body of the apparatus. In this embodiment a compressed purge gas such as instrument quality air is continuously supplied to the pipe interface 14 interconnecting two-way valve 12 with accumulator chamber 2. In this arrangement, chamber 2 is continuously pressurized with compressed purge gas at the interface 14 supply pressure and chamber 2 is integral to the barrel 1, thereby enabling the process gas and purge gas temperatures to reach equilibrium within chamber 2. Valve 12 is opened intermittently, thereby allowing compressed purge gas to flow from accumulator chamber 2 into conditioning chamber 3. The conditioning chamber 3 may include baffling 4, fins, tubing and/or similar apparatus to further enhance heat transfer between the barrel wall and the purge gas. The purge gas pressure and conditioning chamber 2 volume are coordinated to a) displace overcome head losses due to friction in the purge gas supply piping upstream of fitting 14 and b) to displace a volume not greater than the volume of the conditioning chamber 3 and c) to ensure accumulated solids are ejected efficiently from the outside surface of the filter element 6 with sufficient energy to exit from chambers 5 and 8 into the process gas stream. The flow of purge gas to conditioning chamber 3 is controlled by valve 12 in conduit 13 which receives purge gas from the accumulator chamber 2 and supply fitting 14. The purge gas pulse duration and frequency are application specific with typical values of 0.3 seconds and one (1) pulse per hour respectively. Selecting the proper timing of the purge gas is critical to ensure that the temperature and humidity within the conditioning chamber have sufficient time to approach equilibrium. During the pulse cycle, gas pressure in chambers 7 and 8 momentarily exceeds the process gas pressure, thereby ejecting accumulated solids from filter exterior surface into the process gas stream. A conduit 11 carries the necessary signal conductors between the humidity sensor element 9 and a remote system controller (not shown).

Figure 3:
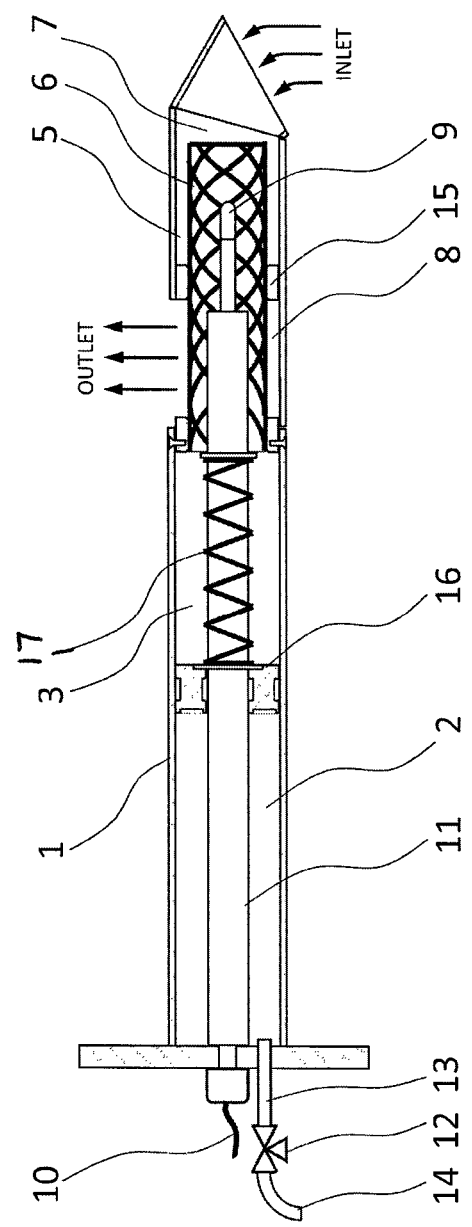
FIG. 3 is a plan cross-section view of an alternate embodiment.

The second embodiment of this invention is illustrated in the cross sectional diagram of FIG. 3. Referring to FIG. 3, a filtration duct 5 houses a filter assembly 6. The filter assembly 6 is comprised of a filter cage and a filter bag, the exterior of which is preferably coated with a PTFE membrane to reduce adhesion of solid particles contained within the process gas. The filtration duct 5 is located in the process gas stream such that a continuous flow of process gas is induced to flow past the humidity sensor element 9 by the differential pressure existing between the high pressure chamber 7 surrounding the filter assembly 6 at the inlet port and the low pressure chamber 8 surrounding the filter assembly 6 at the outlet port. The high pressure chamber 7 and low pressure chamber 8 are separated by a barrier 15 surrounding the exterior of the filter assembly 6. The aforementioned components are joined to other elements within a cylindrical barrel 1 which forms the main body of the apparatus. Chamber 2 is separated from chamber 3 by a piston 16. Chamber 3 is common and contiguous to the internal volume of filter assembly 6. Chamber 2 is intermittently pressurized by a compressed gas such as instrument quality air, thereby displacing piston 16 into chamber 3. Displacement of piston 16 forces process gas contained within chamber 3 outward through filter assembly 6 thereby ejecting accumulated solids from the filter exterior surface into the process gas stream. Following displacement of piston 16 through chamber 3, pressure within chamber 2 is relieved through three-way valve 12 thereby permitting a resistive force applied by spring (or similar energy storage device) 17 to return the piston 16 to its initial position within chamber 2. The compressed gas pressure, chamber 2 volume and pressurization/depressurization cycle times are selected to provide the forces and volume necessary to a) overcome friction and displace piston 16 against the spring 17 force and b) to displace a volume approximately equal to the internal volume of filter assembly 6 and c) to ensure accumulated solids are ejected efficiently from the outside surface of the filter element 6 with sufficient energy to exit from chambers 5 and 8 into the process gas stream. A conduit 11 carries the necessary signal conductors between the humidity sensor element 9 and a remote system controller (not shown).

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A device for sensing humidity in a stream of process gas, comprising:
    elongate cylindrical barrel constituting a main body of the device, said barrel including a process gas inlet port and an outlet port, said outlet port being in fluid communication with said inlet port through a filtration duct, said ports located within the process gas stream so as to conduct a continuous flow of a slip stream of said process gas stream past a humidity sensor;
    a filtration assembly comprising a filter defining an enclosed internal volume housing the humidity sensor, said assembly providing said sensor with a protective barrier against contact with solid matter within said process slip stream;
    a source of purge gas;
    a purge gas conditioning chamber within said barrel partially defined by a sidewall thereof, said chamber being so disposed as to receive a flow of purge gas originating from said source at a first end and to equalize the purge gas temperature and humidity approximately with the process gas stream by direct contact between the purge gas and the slip stream gas; and
    valve means for discharging said purge gas from a second end of said conditioning chamber into said filter internal volume thereby reversing the gas flow direction through the filter to clean the outer surface of the filter.

2. The device of claim 1 further including a purge gas accumulator within said barrel temporarily holding a volume of pressurized purge gas from said source between purge gas pulses and being in fluid communication with said conditioning chamber such that said purge gas is dischargeable from said accumulator into the first end of the conditioning chamber though the valve means.

3. The device of claim 2 wherein the inlet port is located at a distal end of the barrel at an upstream side facing the process stream and the outlet port is laterally disposed through the barrel open to the process gas stream on a downstream side opposite to the inlet port.

4. The device of claim 2 further described in that said accumulator and said conditioning chamber are contiguously situated in longitudinal axial alignment within said barrel.

5. The device of claim 1 further including a baffle within said conditioning chamber thereby enhancing heat transfer from the sidewall to the purge gas.

6. The device of claim 5 wherein said baffle is further described as a spiral helix having a periphery in contact with the wall of the barrel along the entire length of the helix.

7. The device of claim 6 wherein the process gas is power plant combustion flue gas.

8. The device of claim 7 wherein the barrel is disposed perpendicularly to the stream of flue gas.

9. The device of claim 2 wherein said valve means are operable to discharge said purge gas into said conditioning chamber during a pulse cycle at the rate of one cycle per hour, each pulse having a duration of approximately 0.3 seconds.

10. The device of claim 9 wherein said pulse cycle is regulated by a remote controller which is also electrically connected to the humidity sensor.

11. The device of claim 1 wherein the outside of said filter is coated with a PTFE membrane.

12. A device for sensing humidity in a stream of process gas, comprising:
    an elongate cylindrical barrel constituting a main body of the device, said barrel including a process gas inlet port and an outlet port, said outlet port being in fluid communication with said inlet port through a filtration duct operative to conduct a flow path of a slip stream of said process gas stream past a humidity sensor without auxiliary induction means;
    a filtration assembly located within the filtration duct comprising a filter defining a enclosed internal volume within the filter housing the humidity sensor, said assembly providing said sensor with a protective barrier against contact with solid particulate matter within said process gas sample portion; and
    a piston within said barrel in fluid communication with said filter internal volume operative to provide a bi-directional displacement of purge gas to the internal volume of the filter assembly to clean the filter.

13. The device of claim 12 further including a source of compressed air for actuating said piston.

14. The device of claim 13 further including spring means acting upon the piston to move the piston in the direction opposite to the direction of actuation by the compressed air between actuation cycles.

15. The device of claim 2 wherein the purge gas is pulsed into the accumulator from a source of pressurized purge gas during a pulse cycle.

16. The device of claim 15 wherein the pulse cycle is at the rate of one cycle per hour.

17. The device of claim 16 wherein the duration of the pulse is approximately 0.3 seconds.

18. The device of claim 17 wherein said process gas is combustion flue gas.

19. The device of claim 12 wherein said piston is actuated by providing the force necessary to displace a volume of purge gas approximately equal to the internal volume of the filter assembly sufficient to eject accumulated solids on the outside surface of the filter.

20. The device of claim 12 further described in that said piston is reciprocal within a chamber that is contiguous with said internal filter volume such that said purge gas is taken from said process gas slip stream.

21. The device of claim 15 or claim 19 further including the step of adjusting the pulse rate of said pulse cycle to approximate equilibrium between the conditioning chamber gas and the process gas slip stream prior to the initiation of each pulse of purge gas.

22. The device of claim 12 wherein the process gas is power plant combustion flue gas.

23. The device of claim 22 wherein the barrel is disposed perpendicularly to the stream of flue gas.

24. The device of claim 12 wherein the outside of said filter is coated with a PTFE membrane.

25. The device of claim 12 wherein the inlet port is located at a distal end of the barrel at an upstream side facing the process stream and the outlet port is laterally disposed through the barrel on the side opposite to the inlet port.

26. The device of claim 1 wherein the inlet port and outlet port are open to the process gas stream such that a continuous flow of process gas is induced to flow past the humidity sensor by the process gas stream flow without auxiliary induction.

27. The device of claim 12 wherein the inlet port and outlet port are open to the process gas stream such that a continuous flow of process gas is induced to flow past the humidity sensor by the process gas stream flow without auxiliary induction.

28. The device of claim 1 wherein said filtration duct has a high pressure chamber and a low pressure chamber separated by a barrier between the inside of the barrel and the exterior of the filter assembly.

29. The device of claim 12 wherein said filtration duct has a high pressure chamber and a low pressure chamber separated by a barrier between the inside of the barrel and the exterior of the filter assembly.

30. The device of claim 12 wherein the piston lies between first and second chambers, the first chamber is in fluid communication with a source of pressurized gas, and the second chamber is in common with and contiguous to the internal volume of the filter.

* * * * *